(12) United States Patent
Collin et al.

(10) Patent No.: US 7,785,613 B2
(45) Date of Patent: Aug. 31, 2010

(54) FILM-FORMING COSMETIC COMPOSITION

(75) Inventors: Nathalie Collin, Sceaux (FR); Sandrine Olivier, L'Hay les Roses (FR)

(73) Assignee: L'Oreal S.A., Paris (FR)

( * ) Notice: Subject to any disclaimer, the term of this patent is extended or adjusted under 35 U.S.C. 154(b) by 1254 days.

(21) Appl. No.: 10/478,322

(22) PCT Filed: May 21, 2002

(86) PCT No.: PCT/FR02/01705

§ 371 (c)(1), (2), (4) Date: Jun. 14, 2004

(87) PCT Pub. No.: WO02/094206

PCT Pub. Date: Nov. 28, 2002

(65) Prior Publication Data

US 2005/0065253 A1    Mar. 24, 2005

(30) Foreign Application Priority Data

May 21, 2001  (FR) ................................. 01 06657

(51) Int. Cl.
*A61Q 1/10* (2006.01)
*A61Q 1/00* (2006.01)

(52) U.S. Cl. .................... 424/401; 424/61; 424/70.7

(58) Field of Classification Search ................... None
See application file for complete search history.

(56) References Cited

U.S. PATENT DOCUMENTS

| 5,270,461 A | | 12/1993 | Walele et al. |
| 5,271,930 A | * | 12/1993 | Walele et al. ............ 424/78.08 |
| 5,688,493 A | | 11/1997 | Sugawara et al. |
| 5,849,278 A | * | 12/1998 | Piot et al. .................. 424/70.7 |
| 5,858,338 A | | 1/1999 | Piot et al. |
| 6,264,933 B1 | * | 7/2001 | Bodelin et al. ............. 424/70.7 |
| 6,552,212 B2 | * | 4/2003 | Walele et al. ................ 556/437 |

FOREIGN PATENT DOCUMENTS

EP    0 568 035 A2    11/1993

OTHER PUBLICATIONS

French Search Report for PCT/FR 02/01705, dated Oct. 16, 2002.
L.M. Prince, Ed., Microemulsions Theory and Practice, Academic Press, pp. 21-32 (1977).

* cited by examiner

*Primary Examiner*—Jyothsna A Venkat
(74) *Attorney, Agent, or Firm*—Finnegan, Henderson, Farabow, Garrett & Dunner, L.L.P

(57) ABSTRACT

The present disclosure relates to a cosmetic composition comprising, in an aqueous medium, at least one film-forming polymer, at least one aqueous microdispersion of wax, and at least one water-soluble aromatic acid ester that is liquid at room temperature. The present disclosure also relates to the process for cosmetically treating keratinous materials, such as the skin, comprising applying said composition to keratinous materials. The composition is easy to apply on keratinous materials and forms a glossy and non-sticky film.

11 Claims, No Drawings

FILM-FORMING COSMETIC COMPOSITION

The present invention relates to a film-forming composition comprising a film-forming polymer, an aqueous microdispersion of wax and a water-soluble aromatic acid ester. This composition may be used especially in cosmetics for making up or caring for keratin materials such as human skin, eyelashes, nails or hair.

More especially, the composition is a skin makeup composition, for instance an eyeliner, an eyeshadow, a makeup rouge or a body makeup product (semi-permanent tattoo).

Makeup products such as eyeliners and eyeshadows are commonly used for making up the eyes. More and more users are looking for novel makeup products, different from those obtained with standard makeup powders or creamy eyeshadows.

Patent application EP-A-557 196 discloses an eye makeup product comprising a water-soluble film-forming polymer and a wax microdispersion, which forms a shiny makeup. However, such a composition is difficult to apply to the skin: specifically, the film deposited on the skin shrinks during application and does not adhere to the skin immediately on being applied. This composition is therefore unsuitable as an eyeliner or eyeshadow.

To improve the ease of application of the composition, it is possible to add to the composition glycerol or propylene glycol, or alternatively a polydimethylsiloxane silicone containing polyisobutene and lauryl grafts, sold under the name "Dow Corning 2-5276" by the company Dow Corning, but it has been observed that the film then deposited on the skin is too sticky. Now, when an eyeshadow forms a film that is too sticky, the mobile part and the fixed part of the made-up eyelid stick together, which causes the applied makeup to disintegrate and gives the user a very uncomfortable sensation.

For good application of the composition to keratin materials, especially to the skin, it is also possible to add a dimethicone copolyol such as those sold under the names "ABN Silwer" by the company Nippon Uni Care. However, this additive results in a loss of sheen of the film deposited on the skin, thus harming the desired makeup effect.

The aim of the invention is thus to provide a film-forming composition that applies easily to the skin and forms a shiny and non-sticky film thereon.

The inventors have discovered, surprisingly, that the incorporation of a water-soluble aromatic acid ester into a composition comprising a film-forming polymer and an aqueous microdispersion of wax allows very good application, in particular ease of spreading, of the composition onto keratin materials, especially onto the skin, without any shrinkage of the deposited film being observed once the composition has been applied.

In addition, the film formed follows the movement of the skin perfectly without disintegrating.

Furthermore, the composition allows a very shiny and non-sticky film to be obtained. The film obtained after drying also shows good staying power on the skin. Moreover, it is possible to apply onto the dry film another makeup product, especially one having a different colour from that of the film already deposited, while at the same time conserving the colour contrast of each makeup product. The colours of each makeup product applied remain distinct and do not mix, thus allowing highly original coloured effects to be obtained.

More specifically, one subject of the invention is a composition comprising, in an aqueous medium, a film-forming polymer, an aqueous microdispersion of wax and a water-soluble aromatic acid ester that is liquid at room temperature. In particular, the composition according to the invention comprises a physiologically acceptable aqueous medium, i.e. a medium that is compatible with keratin materials such as the skin, for instance a cosmetic medium.

A subject of the invention is also a cosmetic process for making up or for the non-therapeutic care of keratin materials, in particular the skin, comprises the application to the keratin materials of a composition as defined above.

A subject of the invention is also the use of the composition as defined above to obtain a shiny and/or non-sticky film deposited on keratin materials, in particular the skin.

A subject of the invention is also the use of a water-soluble aromatic acid ester that is liquid at room temperature, of a film-forming polymer and of an aqueous microdispersion of wax, in a cosmetic composition comprising an aqueous medium, to obtain a composition that applies and/or spreads easily onto keratin materials, in particular onto the skin, and/or to obtain a shiny and/or non-sticky film deposited on the keratin materials, in particular on the skin.

In particular, the composition according to the invention may comprise a physiologically acceptable aqueous medium, i.e. it may comprise an aqueous medium that is compatible with human keratin materials, for instance an aqueous cosmetic medium.

The term "aqueous microdispersion of wax" means an aqueous dispersion of wax particles, in which the size of the said particles is less than or equal to about 1 μm.

In the present patent application, the wax is a lipophilic compound which is solid at ambient temperature (25° C.), which undergoes a reversible solid/liquid change of state, and which has a melting point of greater than or equal to 30° C. which may be up to 120° C. By bringing the wax to the liquid state (melting), it is possible to make it miscible with oils and to form a microscopically homogeneous mixture, but on returning the temperature of the mixture to the ambient temperature, a recrystallization of the wax in the oils of the mixture is obtained.

The melting point of the wax may be measured using a differential scanning calorimeter (DSC), for example the calorimeter sold under the name DSC 30 by the company Metler. A sample of 15 mg of product placed in a crucible is subjected to a first temperature rise passing from 0° C. to 120° C., at a heating rate of 10° C./minute, and is then cooled from 120° C. to 0° C. at a cooling rate of 10° C./minute and is finally subjected to a second temperature rise passing from 0° C. to 120° C. at a heating rate of 5° C./minute. During the second temperature rise, the variation in the difference in power absorbed by the empty crucible and by the crucible containing the sample of product is measured as a function of the temperature. The melting point of the compound is a value of the temperature corresponding to the top of the peak of the curve representing the variation in the difference in power absorbed as a function of the temperature.

Wax microdispersions are stable dispersions of colloidal wax particles, and are described especially in "Microemulsions Theory and Practice", L. M. Prince Ed., Academic Press (1977) pages 21-32.

In particular, these wax microdispersions may be obtained by melting the wax in the presence of a surfactant, and optionally of some of the water, followed by gradual addition of hot water with stirring. An emulsion of the water-in-oil type is intermediately formed, followed by a phase inversion with final production of a microemulsion of the oil-in-water type. On cooling, a stable microdispersion of solid colloidal wax particles is obtained. Wax microdispersions may also be obtained by stirring the mixture of wax, surfactant and water using a stirring means such as ultrasound, a high-pressure homogenizer or turbomixers.

The particles of the microdispersion of the first wax preferably have average sizes of less than 1 μm (especially ranging from 0.02 μm to 1 μm) and preferably less than 0.5 μm (especially ranging from 0.06 μm to 0.5 μm).

These particles consist essentially of a wax or a mixture of waxes. However, they may also comprise a small proportion of oily and/or pasty fatty additives, a common liposoluble surfactant and/or a common liposoluble additive/active agent.

The waxes which may be used in the compositions according to the invention are chosen from waxes that are solid and rigid at ambient temperature, of animal, plant, mineral or synthetic origin, and mixtures thereof. Preferably, the waxes included in the composition may have a melting point of greater than about 45° C. and in particular greater than 55° C. The wax may also have a hardness ranging from 0.05 MPa to 15 MPa and preferably ranging from 6 MPa to 15 MPa. The hardness is determined by measuring the compressive force, measured at 20° C. using a texturometer sold under the name TA-TX2i by the company Rheo, equipped with a stainless steel cylinder 2 mm in diameter travelling at a measuring speed of 0.1 mm/s, and penetrating into the wax to a penetration depth of 0.3 mm. To carry out the hardness measurement, the wax is melted at a temperature equal to the melting point of the wax+20° C. The molten wax is poured into a container 30 mm in diameter and 20 mm deep. The wax is recrystallized at ambient temperature (25° C.) over 24 hours and the wax is then stored for at least 1 hour at 20° C. before carrying out the hardness measurement. The hardness value is the compressive force measured divided by the area of the texturometer cylinder in contact with the wax.

Mention may be made especially of hydrocarbon-based waxes, for instance beeswax, lanolin wax and Chinese insect waxes; rice wax, carnauba wax, candelilla wax, ouricurry wax, esparto grass wax, cork fibre wax, sugarcane wax, Japan wax and sumach wax; montan wax, microcrystalline waxes, paraffins and ozokerite; polyethylene waxes, the waxes obtained by Fisher-Tropsch synthesis, and waxy copolymers, and also esters thereof.

Mention may also be made of the waxes obtained by catalytic hydrogenation of animal or plant oils containing linear or branched C8-C32 fatty chains. Among these waxes that may especially be mentioned are hydrogenated jojoba oil, hydrogenated sunflower oil, hydrogenated castor oil, hydrogenated coconut oil and hydrogenated lanolin oil.

Mention may also be made of silicone waxes and fluoro waxes.

It is also possible to use commercial mixtures of self-emulsifying waxes containing a wax and surfactants. The wax sold under the name "Cire Auto Lustrante OFR" by Tiscco, which contains carnauba wax and paraffin wax combined with nonionic surfactants, or the self-emulsifying wax sold under the name "Cerax A.O. 28/B" by La Ceresine, which contains esparto grass wax combined with a nonionic surfactant, may be used, for example. These commercial mixtures make it possible to prepare wax microdispersions simply by adding water.

Mention may also be made of the "Aquacer" products from Byk Cera, and especially: the mixture of synthetic and natural waxes with an anionic emulsifier (Aquacer 520), polyethylene wax with a nonionic emulsifier (Aquacer 514 or 513), and polymer wax with an anionic emulsifier (Aquacer 511). Mention may also be made of the mixture of polyethylene wax and of paraffin wax with a nonionic emulsifier, "Jonwax 120" from Johnson Polymer.

The wax may be present in the composition according to the invention in a solids content ranging from 0.1% to 50% by weight, preferably from 0.5% to 30% by weight and better still from 1% to 20% by weight relative to the total weight of the composition.

The composition may also comprise an amount of surfactant which is sufficient to allow a wax microdispersion and a stable final composition to be obtained. It may especially comprise 0.01% to 30% by weight of common surfactant, which may be chosen from the following compounds:

anionic surfactants, especially optionally unsaturated fatty acid salts containing, for example, 12 to 18 carbon atoms; alkaline salts or salts of organic bases of alkylsulphuric and alkylsulphonic acids containing 12 to 18 carbon atoms or of alkylarylsulphonic acids in which the alkyl chain contains 6-18 carbon atoms; sulphate ethers;

nonionic surfactants, especially polyalkoxylated and/or polyglycerolated surfactants, and in particular fatty acids or fatty acid amides; fatty alcohols or alkylphenols; fatty acid esters of polyols; alkanediols and alkyl ethers of alkanediols. Mention may also be made of triglyceryl alkyl carbamates, oxyethylenated or propoxylated derivatives of lanolin alcohols, of lanolin fatty acids, or of mixtures thereof;

cationic surfactants, especially quaternary ammonium derivatives.

The wax or mixture of waxes may be combined with one or more fatty additives (oily and/or pasty). Mention may be made especially of plant oils, for instance sunflower oil or jojoba oil; mineral oils, for instance liquid paraffin; silicone oils; petroleum jelly or lanolin; fluoro oils; hydrocarbon-based oils containing a perfluoro group; fatty alkyl esters.

It is possible also to introduce into the microparticulate waxy phase liposoluble active ingredients, such as UV screening agents, liposoluble vitamins or liposoluble cosmetic active agents.

The film-forming polymer present in the composition according to the invention may be a polymer dissolved or dispersed in the form of solid particles in the aqueous phase of the composition. The composition may comprise a mixture of these polymers.

The film-forming polymer may be present in the composition according to the invention in a solids content ranging from 0.1% to 60% by weight, preferably from 0.5% to 40% by weight and better still from 1% to 30% by weight relative to the total weight of the composition.

In the present patent application, the expression "film-forming polymer" means a polymer which is capable of forming, by itself or in the presence of a film-forming auxiliary agent, a continuous film which adheres to a support, especially to keratin materials.

Among the film-forming polymers which may be used in the composition of the present invention, mention may be made of synthetic polymers, of free-radical type or of polycondensate type, polymers of natural origin, and mixtures thereof.

The expression "free-radical film-forming polymer" means a polymer obtained by polymerization of monomers containing unsaturation, especially ethylenic unsaturation, each monomer being capable of homopolymerizing (unlike polycondensates).

The film-forming polymers of free-radical type may especially be vinyl polymers or copolymers, especially acrylic polymers.

The vinyl film-forming polymers may result from the polymerization of monomers containing ethylenic unsaturation having at least one acid group and/or esters of these acid monomers and/or amides of these acid monomers.

Monomers bearing an acid group which may be used include α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acid monomers are advantageously chosen from the esters of (meth)acrylic acid (also known as (meth) acrylates), especially alkyl (meth)acrylates, in particular of a $C_1$-$C_{30}$ and preferably a $C_1$-$C_{20}$ alkyl, aryl (meth)acrylates, in particular of a $C_6$-$C_{10}$ aryl, and hydroxyalkyl (meth)acrylates, in particular of a $C_2$-$C_6$ hydroxyalkyl.

Among the alkyl (meth)acrylates which may be mentioned are methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates which may be mentioned are hydroxyethyl acrylate, 2-hydroxypropyl acrylate, hydroxyethyl methacrylate and 2-hydroxypropyl methacrylate.

Among the aryl (meth)acrylates which may be mentioned are benzyl acrylate and phenyl acrylate.

The (meth)acrylic acid esters that are particularly preferred are the alkyl (meth)acrylates.

According to the present invention, the alkyl group of the esters may be either fluorinated or perfluorinated, that is to say that some or all of the hydrogen atoms of the alkyl group are replaced with fluorine atoms.

Amides of the acid monomers which may be mentioned, for example, are (meth)acrylamides, and especially N-alkyl (meth)acrylamides, in particular of a $C_2$-$C_{12}$ alkyl. Among the N-alkyl(meth)acrylamides which may be mentioned are N-ethylacrylamide, N-t-butylacrylamide, N-t-octylacrylamide and N-undecyl-acrylamide.

The vinyl film-forming polymers may also result from the homopolymerization or copolymerization of monomers chosen from vinyl esters and styrene monomers. In particular, these monomers may be polymerized with acid monomers and/or esters thereof and/or amides thereof, such as those mentioned above.

Examples of vinyl esters which may be mentioned are vinyl acetate, vinyl neodecanoate, vinyl pivalate, vinyl benzoate and vinyl t-butylbenzoate.

Styrene monomers which may be mentioned are styrene and α-methylstyrene.

The list of monomers given is not limiting, and it is possible to use any monomer known to those skilled in the art falling within the categories of acrylic and vinyl monomers (including monomers modified with a silicone chain).

Among the film-forming polycondensates that may be mentioned are polyurethanes, polyesters, polyesteramides, polyamides, epoxyester resins and polyureas.

The polyurethanes may be chosen from anionic, cationic, nonionic or amphoteric polyurethanes, acrylic polyurethanes, polyvinylpyrrolidone urethanes, polyester polyurethanes, polyether polyurethanes, polyureas, polyurea polyurethanes and mixtures thereof.

The polyesters can be obtained, in a known manner, by polycondensation of dicarboxylic acids with polyols, in particular diols.

The dicarboxylic acid can be aliphatic, alicyclic or aromatic. Examples of such acids which may be mentioned are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalenedicarboxylic acid. These dicarboxylic acid monomers can be used alone or in a combination of at least two dicarboxylic acid monomers. Among these monomers, the ones preferably chosen are phthalic acid, isophthalic acid and terephthalic acid.

The diol can be chosen from aliphatic, alicyclic and aromatic diols. The diol preferably used is one chosen from: ethylene glycol, diethylene glycol, triethylene glycol, 1,3-propanediol, cyclohexanedimethanol, 1,4-butanediol. Other polyols which can be used are glycerol, pentaerythritol, sorbitol and trimethylolpropane.

The polyesteramides can be obtained in a similar manner to that for the polyesters, by polycondensation of diacids with diamines or amino alcohols. Diamines which can be used are ethylenediamine, hexamethylenediamine and meta- or para-phenylenediamine. An amino alcohol which can be used is monoethanolamine.

The polyester can also comprise at least one monomer bearing at least one group —$SO_3M$, with M representing a hydrogen atom, an ammonium ion $NH_4^+$ or a metal ion such as, for example, an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such a group —$SO_3M$ can be used in particular.

The aromatic nucleus of the bifunctional aromatic monomer also bearing a group —$SO_3M$ as described above can be chosen, for example, from benzene, naphthalene, anthracene, biphenyl, oxybiphenyl, sulphonylbiphenyl and methylenebiphenyl nuclei. Examples of bifunctional aromatic monomers also bearing a group —$SO_3M$ which may be mentioned are: sulphoisophthalic acid, sulphoterephthalic acid, sulphophthalic acid, 4-sulphonaphthalene-2,7-dicarboxylic acid.

Copolymers based on isophthalate/sulphoisophthalate, and more particularly copolymers obtained by condensation of diethylene glycol, cyclohexanedimethanol, isophthalic acid and sulphoisophthalic acid, are preferably used. Such polymers are sold, for example, under the brand name Eastman AQ® by the company Eastman Chemical Products.

The polymers of natural origin, which are optionally modified, may be chosen from shellac resin, sandarac gum, dammar resins, elemi gums, copal resins and water-insoluble cellulose polymers, and mixtures thereof.

According to a first embodiment of the composition according to the invention, the film-forming polymer may be present in the form of particles in aqueous dispersion, also known as latices or pseudolatices. The techniques for preparing these dispersions are well known to those skilled in the art. The film-forming polymer particles may have a mean size ranging from 5 nm to 600 nm and preferably from 20 nm to 300 nm.

Aqueous dispersions of film-forming polymer that may be used include the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, and Daitosol 5000® AD by the company Daito Kasey Kogyo; or the aqueous polyurethane dispersions sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer.

Aqueous dispersions of film-forming polymer that may also be used are polymer dispersions resulting from the free-radical polymerization of one or more free-radical monomers inside and/or partially at the surface of pre-existing particles of at least one polymer chosen from the group consisting of polyurethanes, polyureas, polyesters, polyester amides and/or alkyds. These polymers are generally known as hybrid polymers.

According to a second variant of the composition according to the invention, the film-forming polymer may be a water-soluble polymer and is thus present in the aqueous phase of the composition in dissolved form. Examples of water-soluble film-forming polymers that may be mentioned include:
- proteins, for instance proteins of plant origin such as wheat or soybean proteins; proteins of animal origin, such as keratins, for example keratin hydrolysates and sulphonic keratins;
- anionic, cationic, amphoteric or nonionic chitin or chitosan polymers;
- cellulose polymers such as hydroxyethylcellulose, hydroxypropylcellulose, methylcellulose, ethylhydroxyethylcellulose or carboxymethylcellulose, and also quaternized cellulose derivatives;
- acrylic polymers or copolymers, such as polyacrylates or polymethacrylates;
- vinyl polymers, for instance polyvinylpyrrolidones, copolymers of methyl vinyl ether and of maleic anhydride, the copolymer of vinyl acetate and of crotonic acid, copolymers of vinylpyrrolidone and of vinyl acetate; copolymers of vinylpyrrolidone and caprolactam; polyvinyl alcohol;
- optionally modified polymers of natural origin, such as:
- gum arabics, guar gum, xanthan derivatives and karaya gum;
- alginates and carrageenans;
- glycoaminoglycans, and hyaluronic acid and its derivatives;
- shellac resin, sandarac gum, dammar resins, elemi gums and copal resins;
- deoxyribonucleic acid;
- muccopolysaccharides such as hyaluronic acid and chondroitin sulphate, and mixtures thereof.

In the present patent application, the expression "water-soluble aromatic acid ester" means an ester formed from an aromatic acid and from an alcohol, the said ester being soluble in water at 25° C. to at least 50%.

The ester is liquid at room temperature, i.e. at 25° C.

The aromatic acid may be chosen from the following carboxylic acids:
a) monoacids, such as benzoic acid, phenylacetic acid, cinnamic acid, 3-phenylpropanoic acid or salicylic acid;
b) diacids such as terephthalic acid;
c) triacids such as trimellitic acid; and
d) tetracids such as pyromellitic acid.

The aromatic carboxylic acid is advantageously benzoic acid.

The water-soluble aromatic acid ester may advantageously result from the esterification with an aromatic acid (as defined above) of at least one hydroxyl group of a hydroxylated compound chosen from dimethicone copolyols, polyethylene glycol/polypropylene glycol block polymers and polyoxyalkylated methyl glucosides.

Dimethicone copolyols are dimethylpolysiloxanes bearing one or more polyoxyethylene and/or polyoxypropylene side chains.

The polyethylene glycol/propylene glycol block polymers may especially be polyethylene glycol/polypropylene glycol/polyethylene glycol or polypropylene glycol/polyethylene glycol/polypropylene glycol triblock polycondensates. Such block polymers may have a molecular weight ranging from 1000 to 3300. These block polymers may comprise form 10% to 50% by weight of polyethylene glycol, relative to the total weight of the said polymer. Such block polymers are sold especially under the names "Pluronic®" and "Pluronic® R" by the company BASF.

The polyoxyalkylated methylglucosides may be oxyethylenated or oxypropylenated methylglucosides. Such compounds are sold especially under the names "Lucam E" and "Glucam P" by the company Amerchol.

According to a first embodiment of the composition according to the invention, the water-soluble aromatic acid ester may be a dimethicone copolyol benzoate, i.e. an ester, especially a partial ester, of benzoic acid and of dimethicone copolyol, the copolyol being a dimethylpolysiloxane polymer comprising polyoxyethylene and/or polyoxypropylene side chains. The term "partial ester" means a compound in which some of the hydroxyl groups are esterified. Dimethicone copolyol benzoates which may be used include those sold under the name "Finsolv® SLB-101" and "Finsolve SLB-201" by the company Finetex.

According to a second embodiment of the composition according to the invention, the water-soluble aromatic acid ester may be a polyethylene glycol/polypropylene glycol block copolymer benzoate, especially a benzoate of polyethylene glycol/polypropylene glycol/polyethylene glycol or polypropylene glycol/polyethylene glycol/polypropylene glycol triblock polycondensates. Such benzoates are described in patent U.S. Pat. No. 5,271,930. Such compounds correspond especially to the formulae (III) and (IV) below:

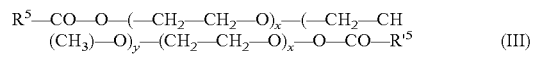

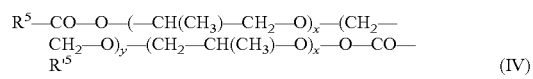

in which:
R$^5$ and R$^{'5}$ denote, independently of each other, a hydrogen atom or a phenyl radical, at least one of the radicals R$^5$ or R$^{'5}$ denoting a phenyl radical, x and y denoting, independently of each other, a number ranging from 2 to 100 and preferably ranging from 2 to 30.

Benzoates of polyethylene glycol/polypropylene glycol block copolymers that may be used include those sold under the "Finsolv® PL-62" and "Finsolv® PL-355" by the company Finetex.

According to a third embodiment of the composition according to the invention, the water-soluble aromatic acid ester may be an oxyethylenated or oxypropylenated methylglucoside benzoate, such as those described in patent U.S. Pat. No. 5,270,461. Such compounds correspond especially to formulae (I) and (II) below:

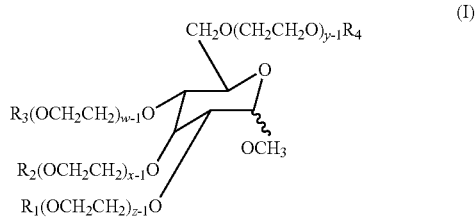

-continued

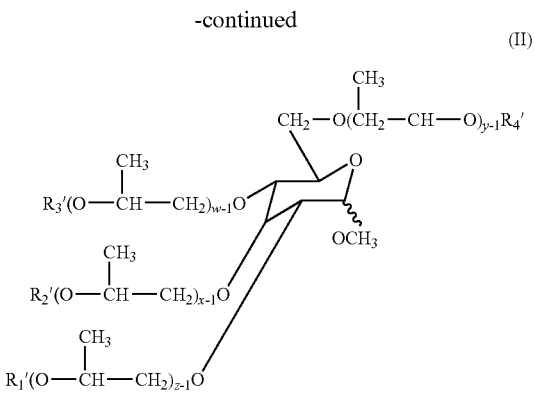
(II)

in which:

$R_1$, $R_2$, $R_3$ and $R_4$ denote

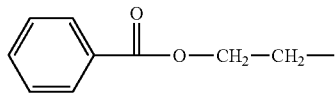

$R'_1$, $R'_2$, $R'_3$ and $R'_4$ denote

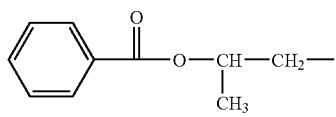

and w+x+y+z ranges from 10 to 20.

An alkoxymethyl glucoside benzoate that may be used is the product sold under the trade name "Finsolv® EMG-20" by the company Finetex.

Preferably, the water-soluble aromatic acid ester is chosen from dimethicone copolyol benzoate and the benzoates of polyethylene glycol/polypropylene glycol block copolymer defined above.

Advantageously, the water-soluble aromatic acid ester is not a methyl glucose benzoate oxyethylenated with 20 ethylene oxide units.

The water-soluble aromatic acid ester may be present in the composition according to the invention in a content ranging from 0.1% to 20% by weight, preferably ranging from 1% to 15% by weight and better still ranging from 5% to 15% by weight, relative to the total weight of the composition.

Advantageously, the film-forming polymer and the aromatic acid ester may be present in the composition in a film-forming polymer/aromatic acid ester weight ratio ranging from 0.1 to 3 and preferably ranging from 0.5 to 2.5.

The aqueous medium of the composition may consist essentially of water. It may also comprise a mixture of water and of water-miscible solvent, for instance lower monoalcohols containing from 1 to 5 carbon atoms, such as ethanol or isopropanol, glycols containing from 2 to 8 carbon atoms, such as propylene glycol, ethylene glycol, 1,3-butylene glycol or dipropylene glycol, $C_3$-$C_4$ ketones, or $C_2$-$C_4$ aldehydes. The aqueous medium (water and optionally the water-miscible organic solvent) may represent, in practice, from 5% to 90% by weight relative to the total weight of the composition.

The composition may also comprise at least one dyestuff, for instance pulverulent compounds, for example in a proportion of from 0.01% to 50% of the total weight of the composition. The pulverulent compounds may be chosen from the pigments and/or nacres usually used in cosmetic compositions. Advantageously, the pulverulent compounds represent from 0.1% to 25% of the total weight of the composition and better still from 1% to 20%.

The pigments may be white or coloured, and mineral and/or organic. Among the mineral pigments which may be mentioned are titanium dioxide, optionally surface-treated, zirconium oxide or cerium oxide, and iron oxide or chromium oxide, manganese violet, ultramarine blue, chromium hydrate and ferric blue. Among the organic pigments which may be mentioned are carbon black, pigments of D & C type, and lacquers based on cochineal carmine or on barium, strontium, calcium or aluminium.

The nacreous pigments may be chosen from white nacreous pigments such as mica coated with titanium or with bismuth oxychloride, coloured nacreous pigments such as titanium mica with iron oxides, titanium mica with, especially, ferric blue or chromium oxide, titanium mica with an organic pigment of the abovementioned type, and nacreous pigments based on bismuth oxychloride.

The composition may also comprise fillers which may be chosen from those that are well known to those skilled in the art and which are commonly used in cosmetic compositions. The fillers may be mineral or organic, and lamellar or spherical. Mention may be made of talc, mica, silica, kaolin, Nylon powder (Orgasol from Atochem), poly-β-alanine powder and polyethylene powder, Teflon, lauroyllysine, starch, boron nitride, tetrafluoroethylene polymer powders, hollow microspheres such as Expancel (Nobel Industrie), Polytrap (Dow Corning), silicone resin microbeads (Tospearls from Toshiba, for example), precipitated calcium carbonate, magnesium carbonate and hydrocarbonate, hydroxyapatite, hollow silica microspheres (Silica Beads from Maprecos), glass or ceramic microcapsules, metal soaps derived from organic carboxylic acids containing from 8 to 22 carbon atoms and preferably from 12 to 18 carbon atoms, for example zinc, magnesium or lithium stearate, zinc laurate or magnesium myristate.

The composition according to the invention may also contain ingredients that are commonly used in cosmetics, such as trace elements, softeners, sequestering agents, fragrances, oils, silicones, thickeners, vitamins, proteins, ceramides, plasticizers, coalescers and cohesion agents, and also the acidifying or basifying agents usually used in cosmetics, emollients and preserving agents.

The composition according to the invention may be a cosmetic composition, which may be in the form of an eyeliner, an eyeshadow, a body makeup product, a lip product, a mascara, a nail varnish, a foundation, an eyebrow product, a haircare product or a skincare product.

Needless to say, a person skilled in the art will take care to select this or these optional additional compounds, and/or the amount thereof, such that the advantageous properties of the composition according to the invention are not, or are not substantially, adversely affected by the envisaged addition.

The composition according to the invention may be prepared according to the usual methods of the fields under consideration.

The invention is illustrated in greater detail in the examples which follow.

EXAMPLE 1

A microdispersion of carnauba wax having the composition below was prepared:

| | | |
|---|---|---|
| Carnauba wax | | 27 g |
| Polyoxyethylenated (30 EO) glyceryl monostearate (Tagat S from Goldschmidt) | | 6.7 g |
| Ethanol | | 10 g |
| Water | qs | 100 g |

The wax and the surfactant were heated to 95° C. while homogenizing the mixture with moderate stirring. Next, the water heated to 95° C. was incorporated with continued stirring. The mixture was cooled to ambient temperature and the ethanol was added to obtain a wax microdispersion with a mean particle diameter of about 170 nm.

EXAMPLE 2

An eyeliner having the composition below was prepared:

| | | |
|---|---|---|
| Wax microdispersion of Example 1 | | 24 g |
| Ethyl alcohol | | 3 g |
| Sulfopolyester sold under the name Eastman AQ 55S by the company Eastman Chemical | | 11 g |
| Dimethicone copolyol benzoate sold under the name "Finsolv SLB-101" by the company Finetex | | 9.5 g |
| Surfactant sold under the name "Symperonic ® PE/L 44" by the company ICI | | 5 g |
| Black iron oxide | | 20 g |
| Preserving agents | qs | |
| Water | qs | 100 g |

This eyeliner applies very easily to the skin and leaves a very shiny, non-sticky film thereon, after drying.

EXAMPLE 3

An eyeshadow having the composition below was prepared:

| | | |
|---|---|---|
| Wax microdispersion of Example 1 | | 53.7 g |
| Ethanol | | 5.9 g |
| Sulfopolyester (AQ 55S from Eastman Chemical) | | 7.6 g |
| Dimethicone copolyol benzoate sold under the name "Finsolv SLB-101" by the company Finetex | | 9.5 g |
| Cyclopentadimethylsiloxane | | 3.6 g |
| Pigments | | 4.8 g |
| Preserving agents | qs | |
| Water | qs | 100 g |

This eyeshadow spreads instantaneously onto the eyelid and forms, after drying, a very shiny, non-sticky film-forming makeup that is comfortable for the user.

EXAMPLE 4

An eyeshadow having the composition below was prepared:

| | | |
|---|---|---|
| Wax microdispersion of Example 1 | | 33 g |
| Ethanol | | 4.5 g |
| Sulfopolyester (AQ 55S from Eastman Chemical) | | 10.5 g |
| Oxypropylenated (30 PO) oxyethylenated (8 EO) polyethylene glycol dibenzoate (8 EO) sold under the name "Finsolv PL-62" by the company Finetex | | 12.3 g |
| Pigments | | 10 g |
| Preserving agents | qs | |
| Water | qs | 100 g |

This eyeshadow spreads instantaneously onto the eyelid and forms, after drying, a shiny film-forming makeup that is comfortable for the user.

EXAMPLE 5

An eyeshadow having the composition below was prepared:

| | | |
|---|---|---|
| Wax microdispersion of Example 1 | | 33 g |
| Ethanol | | 4.5 g |
| Sulfopolyester (AQ 55S from Eastman Chemical) | | 10.5 g |
| Oxypropylenated (16 PO) oxyethylenated (11 EO) polyethylene glycol dibenzoate (11 EO) sold under the name "Finsolv PL-355" by the company Finetex | | 12.3 g |
| Pigments | | 10 g |
| Preserving agents | qs | |
| Water | qs | 100 g |

This eyeshadow spreads instantaneously onto the eyelid and forms, after drying, a shiny film-forming makeup that is comfortable for the user.

The invention claimed is:

1. A composition comprising, in an aqueous medium, at least one film-forming polymer, at least one aqueous microdispersion of wax, and at least one water-soluble aromatic acid ester that is liquid at room temperature,
wherein:
the composition is chosen from eyeliners and eyeshadows;
the at least one water-soluble aromatic acid ester is dimethicone copolyol benzoate and is present in the composition in an amount ranging from 5% to 15% by weight, relative to the total weight of the composition;
the at least one film-forming polymer is chosen from sulfopolyester and polyvinyl pyrrolidone, and is present in a solids content ranging from 1% to 30% by weight, relative to the total weight of the composition; and
the at least one aqueous microdispersion of wax comprises wax chosen from beeswax, lanolin wax, Chinese insect waxes, rice wax, carnauba wax, candelilla wax, ouricurry wax, esparto grass wax, cork fiber wax, sugarcane wax, Japan wax, sumach wax, montan wax, microcrystalline waxes, paraffins, ozokerite, polyethylene waxes, the waxes obtained by Fisher-Tropsch synthesis; waxy copolymers and esters thereof; the waxes obtained by catalytic hydrogenation of animal or plant oils comprising linear or branched C8-C32 fatty chains; hydrogenated jojoba oil, hydrogenated sunflower oil, hydrogenated castor oil, hydrogenated coconut oil, hydrogenated lanolin oil; silicone waxes; and mixtures thereof;

and further wherein the at least one aqueous wax dispersion is present in a wax solids content ranging from 1% to 20% by weight, relative to the total weight of the composition.

2. The composition according to claim 1, wherein the at least one wax dispersion further comprises at least one additional ingredient chosen from oily and/or pasty fatty additives and from liposoluble additive/active agents.

3. The composition according to claim 1, further comprising at least one surfactant.

4. The composition according to claim 1, wherein the at least one film-forming polymer is in the form of solid particles dispersed in the aqueous phase.

5. The composition according to claim 1, wherein the at least one film-forming polymer and the at least one water-soluble aromatic acid ester are present in a weight ratio of film-forming polymer/aromatic acid ester ranging from 0.1 to 3.

6. The composition according to claim 5, wherein the at least one film-forming polymer and the at least one water-soluble aromatic acid ester are present in a weight ratio of film-forming polymer/aromatic acid ester ranging from 0.5 to 2.5.

7. The composition according to claim 1, further comprising at least one additive chosen from thickeners, plasticizers, coalescers, fillers, dyestuffs, waxes, surfactants, preserving agents, oils and fragrances.

8. The composition according to claim 1, wherein the composition is a cosmetic composition.

9. A cosmetic process for cosmetically treating skin, comprising applying to the skin a composition according to claim 1.

10. A process for obtaining a shiny and/or non-sticky film deposited on skin comprising applying to the skin a composition according to claim 1.

11. A cosmetic composition comprising, in an aqueous medium, at least one film-forming polymer, at least one aqueous microdispersion of wax, and at least one water-soluble aromatic acid ester that is liquid at room temperature, wherein the at least one film-forming polymer, at least one aqueous microdispersion of wax, and at least one water-soluble aromatic acid ester that is liquid at room temperature are present in the composition in a combined effective amount such that the composition applies and/or spreads easily onto a keratin material, and wherein:
the composition is chosen from eyeliners and eyeshadows;
the at least one water-soluble aromatic acid ester is a dimethicone copolyol benzoate and is present in the composition in an amount ranging from 5% to 15% by weight, relative to the total weight of the composition;
the at least one film-forming polymer is chosen from sulfopolyester and polyvinyl pyrrolidone, and is present in a solids content ranging from 1% to 30% by weight, relative to the total weight of the composition; and
the at least one aqueous microdispersion of wax comprises wax chosen from beeswax, lanolin wax, Chinese insect waxes, rice wax, carnauba wax, candelilla wax, ouricurry wax, esparto grass wax, cork fibre wax, sugarcane wax, Japan wax, sumach wax, montan wax, microcrystalline waxes, paraffins, ozokerite, polyethylene waxes, the waxes obtained by Fisher-Tropsch synthesis; waxy copolymers and esters thereof; the waxes obtained by catalytic hydrogenation of animal or plant oils comprising linear or branched C8-C32 fatty chains; hydrogenated jojoba oil, hydrogenated sunflower oil, hydrogenated castor oil, hydrogenated coconut oil, hydrogenated lanolin oil; silicone waxes; and mixtures thereof;

and further wherein the at least one aqueous wax dispersion is present in a wax solids content ranging from 1% to 20% by weight, relative to the total weight of the composition.

* * * * *